(12) United States Patent
De Vries

(10) Patent No.: US 7,535,569 B2
(45) Date of Patent: May 19, 2009

(54) OPTICAL MEASUREMENT UNIT FOR A MEASUREMENT DEVICE AND A HANDHELD PHOTOELECTRIC MEASUREMENT DEVICE

(75) Inventor: Loris De Vries, Buchs (CH)

(73) Assignee: X-Rite Europe GmbH, Regensdorf (CH)

( * ) Notice: Subject to any disclaimer, the term of this patent is extended or adjusted under 35 U.S.C. 154(b) by 169 days.

(21) Appl. No.: 11/512,541

(22) Filed: Aug. 30, 2006

(65) Prior Publication Data

US 2007/0046279 A1 Mar. 1, 2007

(30) Foreign Application Priority Data

Aug. 31, 2005 (EP) ................................. 05018942

(51) Int. Cl.
*G01N 21/25* (2006.01)
(52) U.S. Cl. ..................................................... 356/418
(58) Field of Classification Search .................. 356/418
See application file for complete search history.

(56) References Cited

U.S. PATENT DOCUMENTS

| | | | |
|---|---|---|---|
| 4,003,660 A | | 1/1977 | Christie, Jr. et al. |
| 5,137,364 A | * | 8/1992 | McCarthy ................... 356/402 |
| 5,168,320 A | * | 12/1992 | Lutz et al. ..................... 356/73 |
| 6,020,583 A | * | 2/2000 | Walowit et al. ............. 250/226 |
| 6,031,617 A | | 2/2000 | Berg et al. |
| 6,369,895 B1 | * | 4/2002 | Keeney ....................... 356/419 |
| 7,262,855 B2 | * | 8/2007 | Van Andel et al. .......... 356/418 |
| 2002/0167669 A1 | | 11/2002 | Schwarz |
| 2003/0132982 A1 | | 7/2003 | Tandon et al. |
| 2003/0169421 A1 | * | 9/2003 | Ehbets ....................... 356/328 |

OTHER PUBLICATIONS

European Search Report dated May 11, 2006.

* cited by examiner

*Primary Examiner*—Kara E Geisel
(74) *Attorney, Agent, or Firm*—McCarter & English, LLP

(57) ABSTRACT

A handheld photoelectric measurement device includes a housing (G) which is provided with a measurement window (F). An illumination arrangement is positioned in the housing for impinging the measurement object through the measurement window with illumination light from two mutually perpendicular directions. The housing further includes an optical pickup arrangement for the capture of the measurement light through the measurement window, a photoelectric converter arrangement provided by the pickup arrangement with the captured measurement light for conversion of the measurement light into corresponding electric measurement signals, and an electronic processing arrangement. The housing (G) is at its forward side provided with a lateral measurement niche (N) which can be opened or closed to the outside by a movable wall portion. The measurement window (F) is freely visible when the measurement niche is opened. Furthermore, a motor drive is provided for movement of the wall portion.

26 Claims, 9 Drawing Sheets

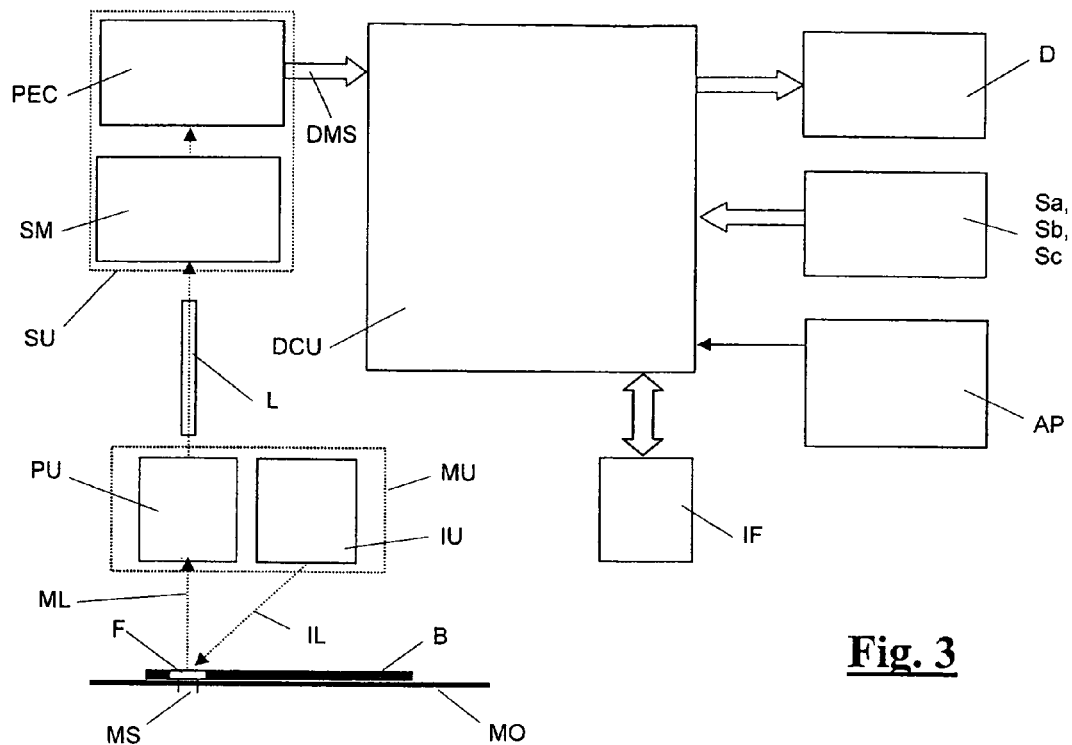
Fig. 3
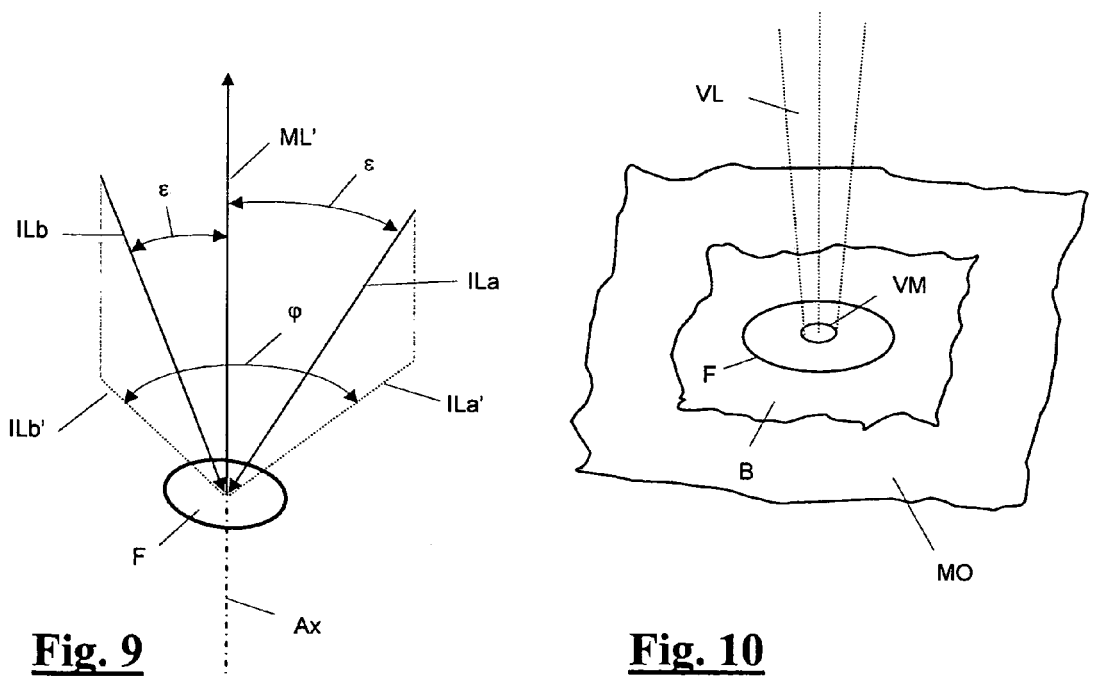
Fig. 9  Fig. 10

OPTICAL MEASUREMENT UNIT FOR A MEASUREMENT DEVICE AND A HANDHELD PHOTOELECTRIC MEASUREMENT DEVICE

BACKGROUND

1. Technical Field

The invention relates to an optical measurement unit for a measurement device for the photoelectric scanning of a measurement object as well as a handheld photoelectric measurement device equipped with such an optical measurement unit. In particular, the invention relates to an optical measurement unit for a colour measurement device, a colour densitometer, a spectrophotometer or a multifunctional device for the quantitative capture of colours as well as to the device itself.

2. Background Art

The term handheld measurement device is understood in the following to be a generally autonomous, portable measurement device, which is normally provided with operating and display elements and is positioned manually at or on the object to be scanned. However, expressly included are also such devices which can be connected through a communication channel with an external device, for example a computer and can exchange measurement and/or control data therewith. In the extreme case, a handheld measurement device in accordance with the invention can include in a housing only an optical measurement unit and a downstream photoelectric converter arrangement.

Known handheld measurement devices of this type are, for example, "SpectroEye" of the company Gretag-Macbeth AG, "Vipdens 2000" of the company Viptronic, "530 SpectroDensitometer" of the company X-Rite and "SpectroDens" of the company Techkon.

Handheld measurement devices of this generic type are used for the spectral and/or densitometric colour measurement in a plurality of applications such as the packaging, newsprint, advertising, security, paint and lacquer industry. The measurable colour palette extends from the classical CMYK print colours through metallized up to highly pigmented ANIVA colours. They can be applied, for example, to substrates such as painted or unpainted paper and transparent or metallized foil. The broad range of applications and the sometimes rough environmental conditions place high demands onto a device used therefor.

A compact, ergonomic and robust construction is a basic requirement of a handheld measurement device for industrial use. Dust and dirt tightness are indispensable for the printing process control in the printing room where paint vapors and printing powder particles are suspended in the air. The measurement result must be as independent from the positioning of the measurement device as possible even for measurement objects with a finely structured and oriented surface structure. The demand for an ever smaller maculation by the printing of colour control fields is directly followed by a reduction in their dimensions. The measurement device must therefore be adaptable by way of an exchangeable measurement aperture to the colour control field size to be measured and must be exactly positionable thereon. Depending on the situation, a measurement without additional filters or with polarization or UV or D65 filters is required.

The mentioned handheld measurement devices currently on the market fulfill these demands to different degrees. A large problem common to all known devices consists however in the sometimes insufficiently precise, sometimes cumbersome positioning of the handheld measurement device on the measurement object, especially when the measurement locations to be scanned are very small.

Because of the often present surface texture of the measurement object, the impinging illumination light is not evenly diffusely remitted so that the measurement result is dependent on the positioning of the measurement device on the measurement object. This is especially the case with oriented illumination arrangements of simple construction. Positioning hereby refers to the rotational position of the measurement device relative to the normal on the measurement object at the measurement location. This problem is often addressed by an annular, which is all around continuous or made of discrete light sources. Because of its construction, it is the nature of an annular (45°/0°) illumination arrangement that the measurement location of the measurement object is covered along its whole circumference during the measurement. If such a measurement arrangement is used in a measurement device, more or less complex mechanisms are required to guarantee a clear line of sight to the measurement object during the positioning.

Several known devices (for example "Vipends 2000" and "530 SpectroDensitomer") are equipped with a pivot mechanism. In the at rest position, in which the positioning of the device on the measurement object is carried out, the device housing is pivoted up relative to a base plate which includes a sighting opening, so that the sighting opening is freely visible. For the measurement, the device housing is then pivoted down, whereby the measurement head of the device is lowered onto the sighting opening. This can result in a shifting of the device so that the positioning is no longer correct. Furthermore, because of the pivot mechanism, such devices are mechanically relatively complex.

Other devices (for example, "SpectroEye") have a motor driven measurement head which is located within the device housing during the at rest position and for the measurement is moved outside thereof and over a protruding sighting opening, and then returned again into the housing after the measurement. This solution is mechanically complex.

Further known devices (for example "SpectroDens") have only a single sighting opening which covers the whole measurement location to be scanned so that the positioning of the measurement device especially with small measurement spots is rendered difficult. This and other devices mostly have a simple oriented illumination arrangement and are mechanically relatively simple. However, because of the absence of a continuous or discrete annular illumination, they have the mentioned measurement technological limitations.

It is now an object of the present invention to improve an optical measurement unit and a handheld measurement device of the generic type in such a way that with the smallest possible constructive cost a positioning independence is largely achieved and a precise positioning on the measurement object is guaranteed without cutbacks in the handling ergonomics.

SUMMARY

The objects underlying the invention are achieved with an optical measurement unit or by a handheld photoelectric measurement device as described herein.

A relatively small range of the angles of incidence (also called "angle of incidence range") means in particular that the lower end of the angle of incidence range is above 35°, especially above 40° or 43°, while the upper end is below 55°, especially below 50° or 47°. A relatively small detection angle range means especially that the angle range extends over less than 20° especially less than 15° or 10° or less than 5°. The mean of the detection angle range lies especially in the range of −5° to +10°. Essentially 90° means in particular that the offset angle lies in a range with an upper limit of 80° or 85° or 88°, and a lower limit of 100° or 95° or 92°.

According to the basic concept of the invention, the illumination of the measurement object is therefor carried out in two directions in space, which are perpendicular to one another. This allows an especially simple constructive implementation of the optical measurement unit and nevertheless leads to positioning independent measurement results sufficient for the practice, which are comparable in most practical applications to those of a continuous or discreet annular illumination.

Preferred embodiments and improvements of the optical measurement unit in accordance with the invention and of the handheld measurement device in accordance with the invention are subject of the dependent claims.

BRIEF DESCRIPTION OF THE FIGURES

The invention is further described in the following by way of the drawings, which show:

FIG. 3 a block diagram of the most important functional units of the handheld measurement device of FIG. 1;

FIG. 9 a schematic for illustration of the path of the illumination beams;

FIG. 10 a schematic for the illustration of an optical sighting light marker;

DESCRIPTION OF EXEMPLARY EMBODIMENT(S)

Figure 1:
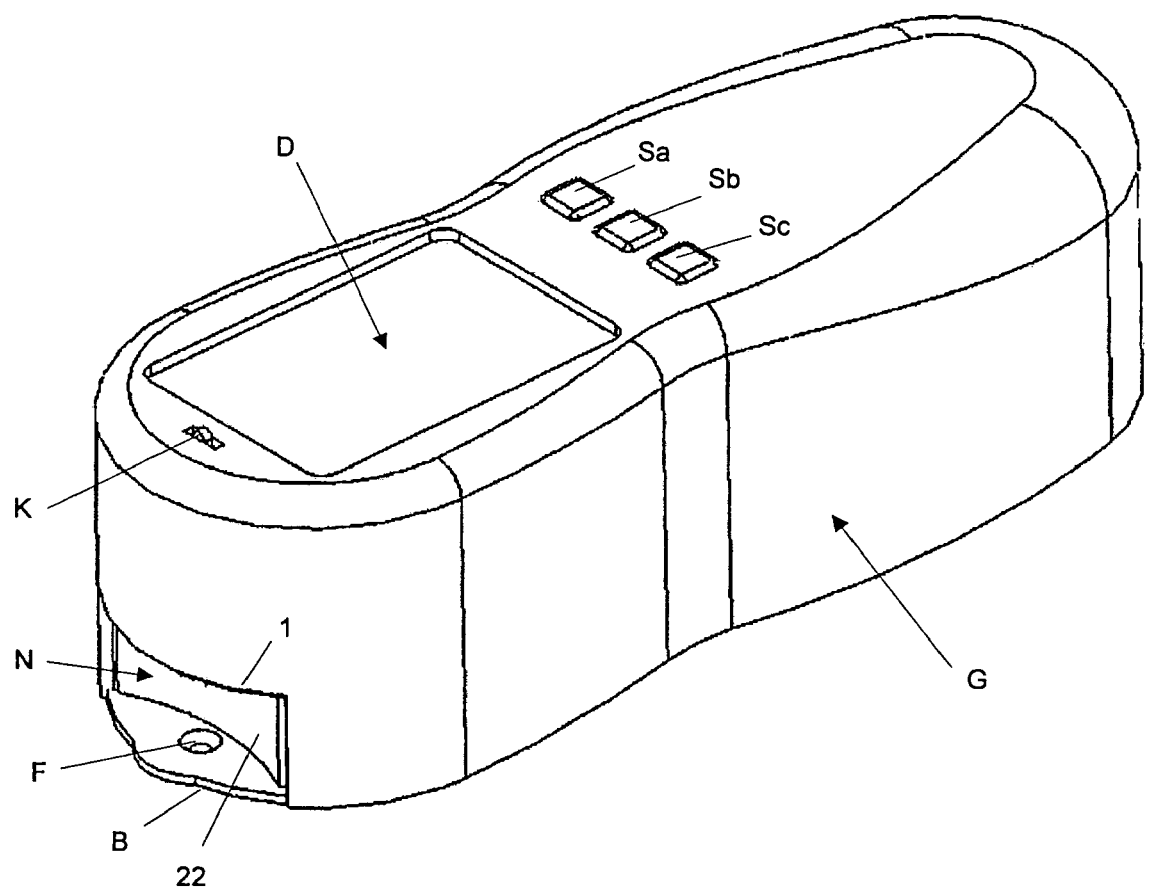
FIG. 1 a perspective view of a typical embodiment of the handheld measurement device in accordance with the invention.
Figure 2:
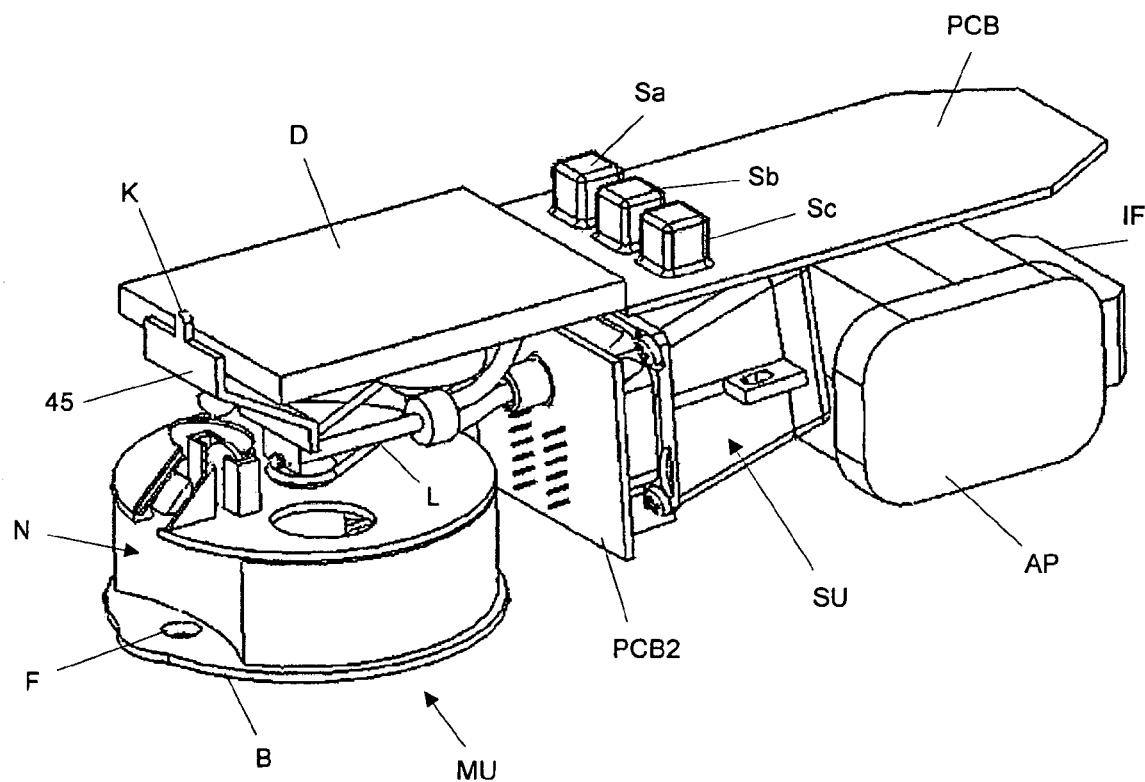
FIG. 2 the handheld measurement device of FIG. 1 without housing.

The outer shape of the handheld measurement device in accordance with the invention, here for example constructed as a spectrophotometer, is apparent from FIG. 1. As is common in a handheld measurement device, all functional units and other elements and constructional units are housed inside or on the surface of a housing G. On the top of the housing G, a display arrangement D and operating elements in the form of three push buttons Sa-Sc and a slide button K are visible. A cutout 1 is positioned on the forward side of the housing behind which is located a measurement space which is here illustrated in the open condition and in the form of a measurement niche N. The measurement niche N can, as further discussed further below, be opened to the inside of the housing and again closed by a movable wall portion. A here not visible interface connector for the connection with an external device is located on the backside of the housing opposite the cutout 1. The interface connector IF is illustrated in FIG. 2. A base plate B is located at the underside of the housing G, which is penetrated in the region of the measurement niche N by a typically circular measurement window F.

For the scanning of a measurement object, the handheld measurement device with opened measurement niche is positioned onto the measurement object in such a way that the measurement location to be scanned is located within the measurement window F. To facilitate an exact positioning, the handheld measurement device is equipped with special sighting means will be further discussed further below.

The most important functional units of the handheld photoelectric measurement device in accordance with the invention as well as their spatial orientation are apparent from FIG. 2, which shows the handheld measurement device without housing, and from the schematic block illustration in FIG. 3. One recognizes an optical measurement unit which is labeled as a whole with MU having an illumination arrangement IU and a detection arrangement PU, a spectrometer unit SU with a spectrometer SM and a photoelectric converter arrangement PEC, the printed circuit board PCB on which is located a (digital) processing and control electronic DCU of the handheld measurement device, a power supply in the form of an accumulator pack AP as well as the already mentioned interface connector IF of the display arrangement D, the three push buttons Sa-Sc and the slide button K. A further printed circuit board PCB2 is mounted on the spectrometer unit SU which carries the electronics associated with the photoelectric converter arrangement PEC and is connected through not illustrated electrical conductors with the circuit board PCB or the processing and control electronic DCU located thereon.

The illumination arrangement IU included in the optical measurement unit MU is constructed for the impinging of a measurement object MO with illumination light IL through the measurement window F. The pickup arrangement PU also included in the optical measurement unit MU captures the measurement light ML remitted by the measurement location MS of the measurement object MO through the measurement window F. A light conductor L guides the captured measurement light ML to the spectrometer unit SU.

The general functioning of the handheld measurement device is as follows: the measurement unit MU impinges the measurement location ML of the measurement object MO with the illumination light IL, captures the measurement light ML remitted from the measurement location and guides it through the light conductor L into the spectrometer unit SU. The measurement light ML is therein split by the spectrometer SM into spectral ranges and converted by way of the photoelectric converter arrangement PEC into corresponding electric (digital) measurement signals DMS. They are guided to the processing and control electronics DCU and processed thereby. The measurement signals or measurement data derived therefrom are displayed by way of the display arrangement D. Alternatively, or additionally, the measurements signals, or measurement data calculated therefrom, can be output to the interface connector IF. All measurement and processing operations are controlled by the processing and control electronics DCU, whereby the user can influence them through the operating elements Sa-Sc. A data exchange or an external control is also possible in a known manner by way of the interface connector IF.

In this general sense, the handheld measurement device in accordance with the invention corresponds in construction and function to the prior art as it is established by, for example, the handheld photoelectric measurement devices on the market as mentioned above. Especially the spectrometer unit SU with the associated photoelectric converter arrangement PEC, the processing and control electronics DCU, the display arrangement D (LCD panel) and the interface connector IF are the same as or analogous to those of known apparatus of this type. Therefore, the person skilled in the art does not need any further description in this respect. The deciding difference between the invention and the state of the art consists first and foremost in the conception of the optical measurement unit MU in accordance with the invention and the arrangement of the measurement window F in an openable and closable measurement space, as will be described in detail in the following.

As is apparent from FIGS. 4 to 8, the optical measurement unit MU in accordance with the invention includes the already mentioned base plate B, a cover plate 10 which is positioned spaced apart parallel thereto and stationary in the housing G and serves as mounting plate, an essentially cylindrical mantel 20 rotatably positioned between the base plate B and the cover plate 10 and having a cylindrical part 21 and an inwardly protruding indentation 22 (or a flattened portion), a pair of illumination light sources in the form of light emitting diodes 31a, 31b, a pair of associated illumination optics in the form of illumination lenses 32a, 32b, a redirecting prism 41, a detection optics in the form of detection lens 42, a coupling lens 43, a movable aperture plate 44 provided with several differently sized focal apertures 44a, a window plate 50 coaxially positioned within the mantel and non-rotatably connected therewith, a drive motor with associated drive belt 61 for the mantel 20, the already mentioned light conductor L formed by a fiber bundle, a sighting light source in the form of a further light emitting diode 71, a further light conductor 72 also formed by a fiber bundle, a coupling lens 73 and a physical white reference 80 which is positioned on the free end of a pivot arm 81 which is suitably coupled to the mantel for limited rotation. With the exception of the mantel 20 with the window plate 50 located therein and the white reference 80 as well as the movable aperture plate 44, all parts are rigidly fixed to the cover plate 10 or at other locations in the housing G. The rotation of the mantel 20 with the window plate 50 therein is controlled by the control and processing arrangement DCU.

Figure 5:
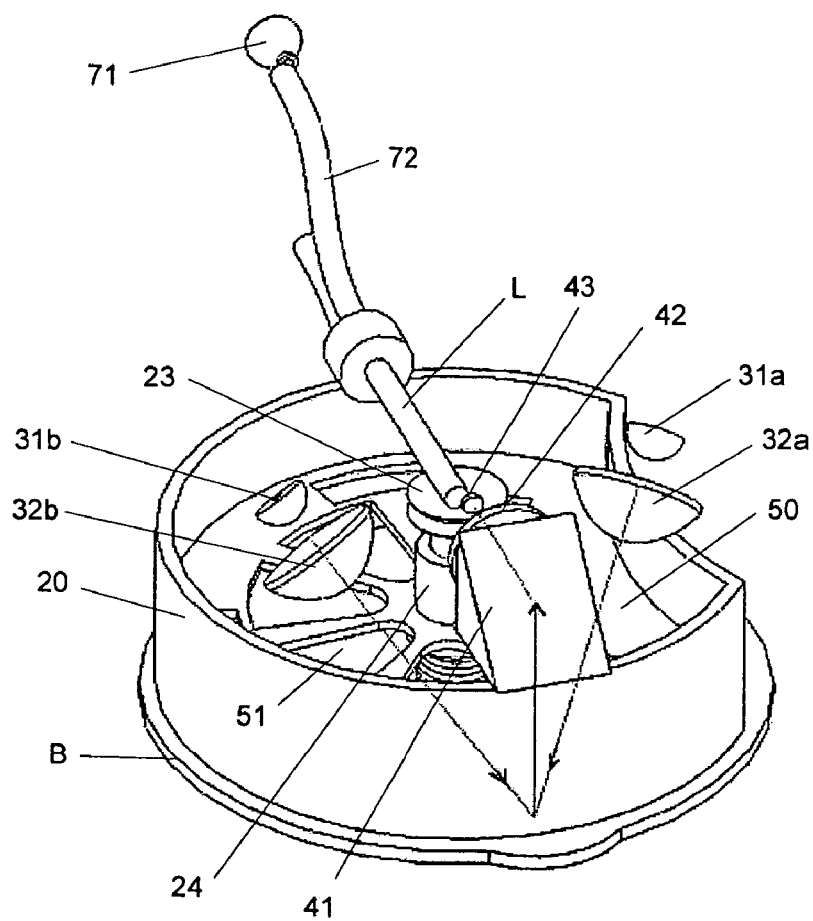
FIGS. 5-7 partial views of the optical measurement unit of FIG. 4.
Figure 6:
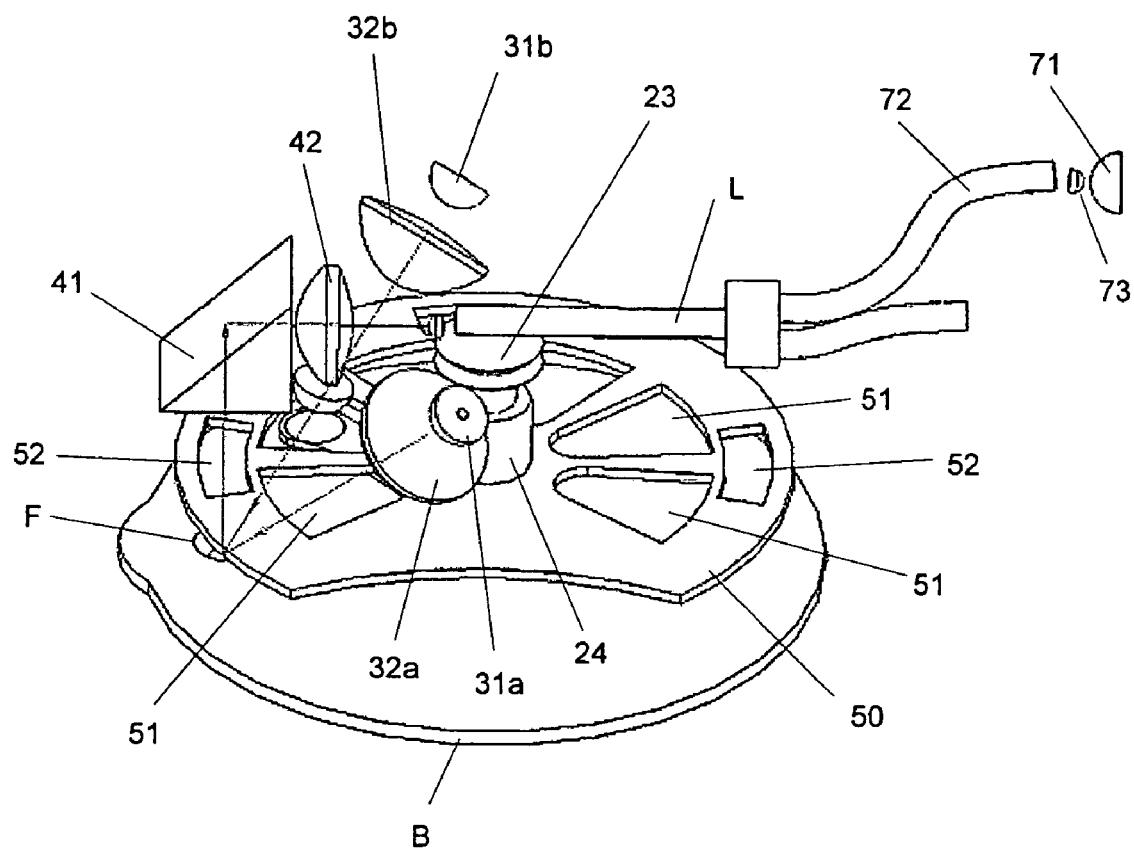
Figure 7:
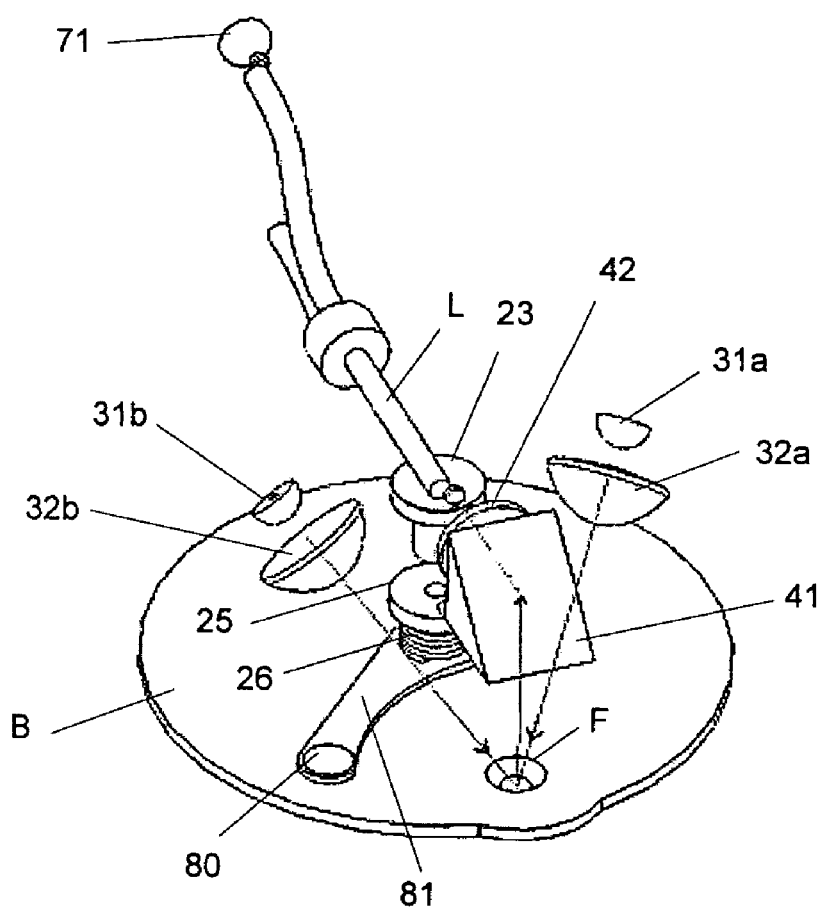

Different parts of the optical measurement unit MU are omitted in FIGS. 5 to 7 in order to render visible those parts which are located therebehind or therebelow and in order to make the constructive details more clearly apparent. The mounting structures for the different light sources and lenses are also not drawn for the same reasons.

Figure 8:
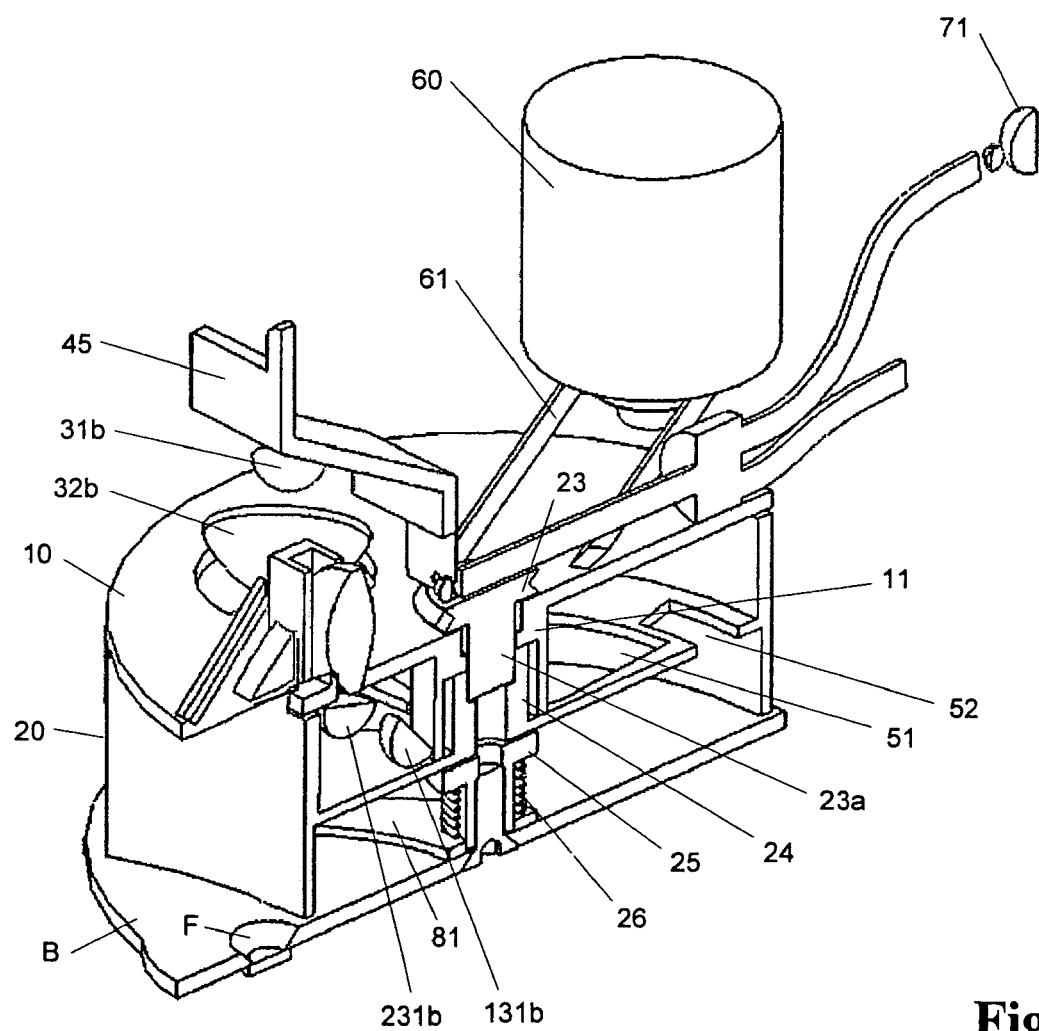
FIG. 8 the optical measurement unit of FIG. 4 in cross-section.

The rotatable support of the mantel 20 is apparent from the cross-sectional illustration of FIG. 8. The motor 60 drives a pulley 23 by way of the belt 61, which pulley is rotatably supported by way of a short axle 23a in a bushing 11 of the cover plate 10. A hub 24 is fixed on the axle 23a and carries the window plate 50 or is a part thereof. Finally, a supporting pipe 25 supports the hub 24 and therefore the window plate 50 on the base plate B.

A first essential aspect of the invention consists in the special construction of the measurement unit MU so that the illumination of the measurement object is carried out from two mutually perpendicular directions in space and obliquely from within the housing G. In the concrete exemplary embodiment, the illumination is carried out through the interior of the mantel 20 and then through the measurement window F. The illumination geometries (illumination angle ranges), which are common for photoelectric measurement devices or standardized, must of course be met. The common standard illumination geometry provides an illumination angle range $\epsilon$ of 45°±5° (relative to the normal on the measurement object at the measurement location), whereby the pickup angle range $\alpha$, under which the measurement light remitted from the measurement object is captured, is then 0°±5° (also with respect to the normal on the measurement object at the measurement location). However, for special applications, other illumination angle ranges are often used, for example 60°±5° or 75°±5° (with respect to the normal on the measurement object at the measurement location), whereby the pickup angle range is again 0°±5°. A further advantageous pickup angle range is for example, 8°±5°. When then additionally a further light source with an illumination angle range of 8°±5° is provided, 8°/8° gloss measurements can be carried out with such a measurement geometry.

It must be considered the crucial point of the illumination geometry of the measurement unit MU in accordance with the invention that respectively a pair of light sources 31a, 31b and associated illumination lenses 32a, 32b is provided, which illuminate the measurement object each under the same illumination angle range $\epsilon$, but from two mutually essentially perpendicular spatial directions. For this, the light sources and illumination lenses are oriented in such a way that the two illumination beam paths produced thereby (at least in the vicinity of the measurement window F, which means upon impinging on the measurement object) are offset from one another by an offset angle $\phi$ of essentially 90°, relative to an axis AX perpendicular to the plane of the measurement window F. This is illustrated in FIG. 9. The (main axis of the) two illumination beam paths are referenced therein with ILa and ILb and their projections onto the plane of the measurement window F with ILa' and ILb'. The angle between the two projections yields the offset angle $\phi$. This spatial angular offset in accordance with the invention results largely in a positioning independence of the measurement result which is practically equal to that of an annular illumination. However, in addition to the positioning independence, the conditions for a simple constructive conversion of many further important functional characteristics of the measurement device are created, especially for its precise positioning.

The illumination lenses 32a, 32b can also be omitted, when the light sources 31a, 31b are positioned very close to the measurement object (measurement window F). The illumination arrangement consists then of the light sources (for example LEDs with transparent housing) and suitably formed light exit openings (apertures).

The two illumination beam paths extend, as already mentioned, through the interior of the mantel 20. The window plate 50 is therefore provided with at least one fittingly sized illumination window 51 through which the illumination light can pass. Preferably, a separate (small) illumination window is provided for each of the two illumination beam paths. According to a preferred embodiment, two or more pairs of illumination windows 51 are provided in circumferential direction one after the other in the window plate 50 and at least some of them are fitted with filters for the manipulation of the illumination light. Such filters can be, for example, color, UV or polarization filters. Filters required for a specific measurement situation can thereby be rotated into the illumination beam paths by corresponding rotation of the mantel 20 and, therefore, the window plate 50. In this preferred embodiment, the window plate 50 has the function of an inherently known filter wheel.

The measurement light ML remitted by the measurement object is captured in the illustrated embodiment by the pickup arrangement of the optical measurement unit MU under a pickup angle range $\alpha$ of 0°±5° (relative to the normal on the measurement window F). A preferred alternative pickup angle range is, for example, 8°±5°. The pickup arrangement consists essentially of the redirecting prism 41, the pickup lens 42, the coupling lens 43 and the aperture plate 44. The redirecting prism 41 is located perpendicular above the measurement window F. In the measurement position of the mantel 20, the remitted measurement light ML passes in the interior of the mantle 20 through a pickup window 52 at the periphery of the window plate 50 and reaches the pickup lens 42 through the redirecting prism 41 and is coupled by way of the coupling lens 43 and through the aperture plate 44 into the light conductor L which then feeds it to the spectrometer unit SU. The window plate 50 preferably has two or more pickup windows 52 along its edge, whereby their number and positioning is coordinated with the number of illumination windows 51 and one pickup window 52 is respectively associated with one pair of illumination windows 51. Therefore, depending on the measurement position (rotational position) of the mantle 20, another illumination window pair and one pickup window are located in the two illumination beam paths or the pickup beam path. Of course, the window plate 50 does not include any windows in the region of the indentation 22 of the mantle 20. Instead of, or in addition to the filters in the illumination windows 51, filters can also be positioned in the pickup windows 52.

When the optical measurement unit MU is to be constructed without filters, the window plate 50 can of course be omitted. In that case, the mantle 20 would have to be connected, for example, by spokes or the like with the hub 23 or rotatably supported in another manner.

The aperture plate 44 is part of an offset slider 45 which at its upper end has the already mentioned slide button K which protrudes from the top surface of the housing and is supported in the housing G for manual back and forth adjustment in direction of the arrow 46. By adjustment of the slider 45 respectively one of the differently sized focal apertures 44a of the aperture plate 44 are brought into the pickup beam path between the coupling lens 43 and the light conductor L. The focal apertures 44a limit the size (diameter) of the measurement region (measurement spot) on the measurement object which is considered for the measurement. In this manner, the measurement device can be easily adjusted to different measurement situations.

The two illumination light sources 31a and 31b can also be selectively switchable on and off (by way of the processing and control electronic DC). This permits the independent measurement from two spatial directions mutually offset by 90° and therefore the detection of a possibly present surface structure of the measurement object and, if necessary, the initiation of corresponding measures.

A further important aspect of the invention consists in the already mentioned measurement space, which is openable and closeable in relation to the housing interior, in the illustrated example constructed as a measurement niche N and the positioning of the measurement window F in the region of this measurement space or this measurement niche. As is illustrated in FIG. 1, the measurement window F is freely visible to the user of the device when the measurement niche N is opened, so that the handheld measurement device can be easily and safely positioned on the measurement object in such a way that the measurement location of the measurement object to be scanned is located within the measurement window. The measurement niche N is then again locked during the measurement in order to avoid external light influences.

Figure 4:
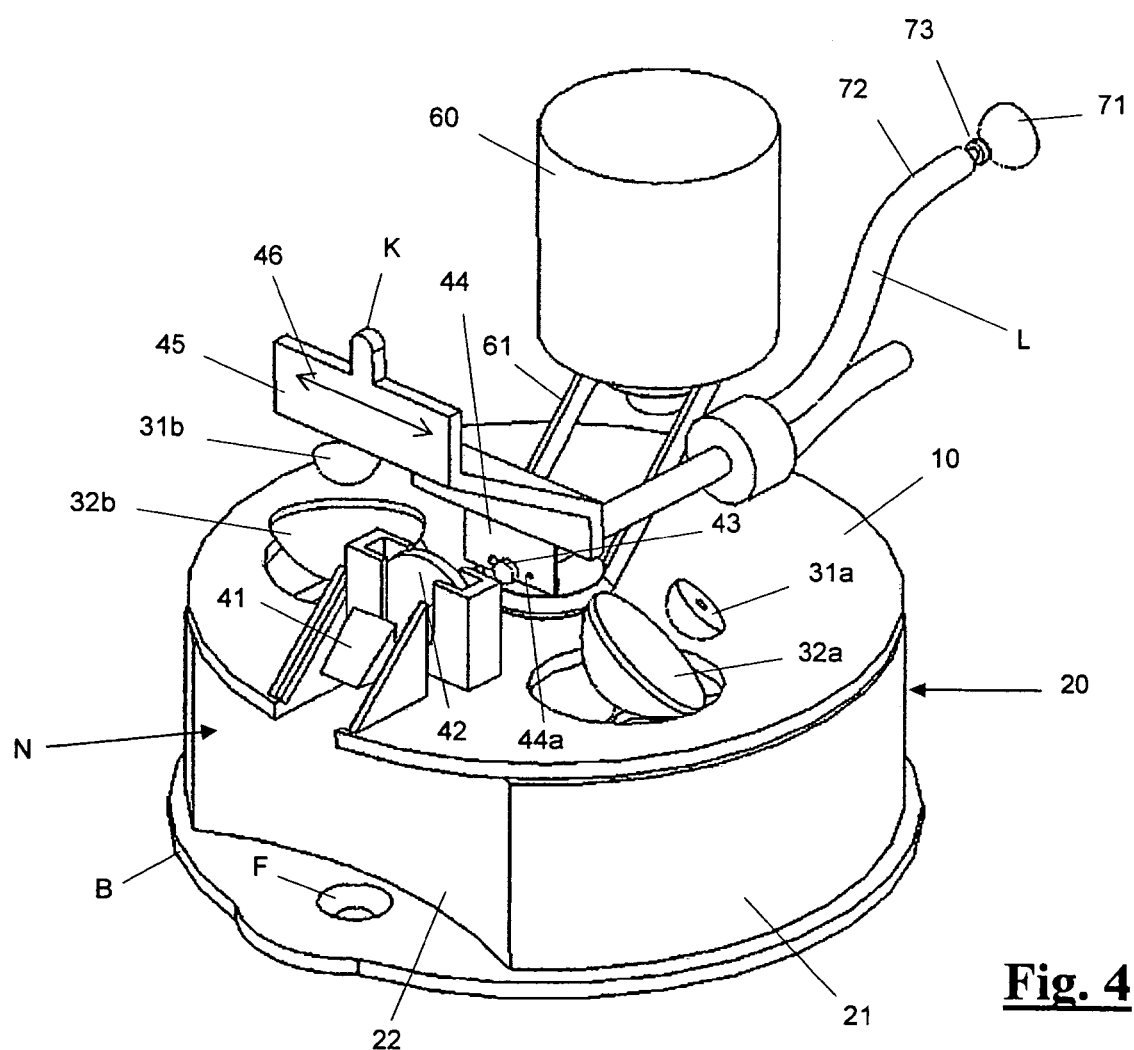
FIG. 4 a perspective view of the optical measurement unit in accordance with the invention of the handheld measurement device according to FIG. 1.

The opening and closing of the measurement niche N is carried out by a movable wall portion which according to a further aspect of the invention is formed by the cylindrical part 21 of the mantle 20 of the optical measurement unit MU. Depending on the rotational position of the mantle 20 either its indentation (or flattened portion) 22 or the cylindrical portion 21 of the mantle 20 is located in front of the cutout 1 in the housing G. The mantle 20 is positioned in the housing in such a way that its cylindrical part 21 normally closes the cutout 1, whereby the measurement window F is then located inward of the mantle 20. The measurement niche N is in that case located within the mantle 20 and closed to the outside. On the other hand, the indentation (or flat portion) 22 of the mantle 20 is sized and shaped such that it is located relative to the housing G inward of the measurement window F when the mantle 20 is rotated is rotated into a position wherein the indentation is in the region of the cutout 1. The measurement niche N is in this case open to the outside, but closed to the interior of the housing by the indentation 22. The infiltration of dust etc. into the housing interior is thereby prevented. FIGS. 1 and 4 show the mantle 20 in a rotational position wherein the measurement niche N is opened to the outside. This rotational position of the mantle 20 is in the following referred to as sighting position. All other rotational positions of the mantle 20 in which the measurement niche is closed to the outside are referred to as measurement positions. One of these rotational positions is illustrated in FIG. 5.

In the illustrated embodiment, the measurement space is located completely within or behind the forward housing wall. However, it is also possible, according to a variant, that the measurement unit MU is positioned in the housing G in such a way that the base plate B extends beyond the forward housing wall, whereby the measurement space is then located wholly or partially outside the forward housing wall. In its measurement positions, the mantle then again closes the measurement space dust and light tight.

The measurement window F serves (in sighting position of the mantle, which means with opened measurement niche N) as a relatively crude sight for the positioning of the measurement device on the desired measurement location of the measurement object. For an improved positioning accuracy, which is important especially for very small measurement locations an additional sighting aid is provided according to a further aspect of the invention in the form of an optical sighting arrangement which projects a sighting light marker VM (FIG. 10) through the measurement window F onto the measurement object, which optically marks the exact position of the measurement region on the measurement object captured by the pickup arrangement. The optical sighting arrangement can be constructed in any way, since only a sighting light source and a compatible projection arrangement are required for its realization. However, according to an especially advantageous embodiment of the invention, the pickup arrangement is used for the projection of the sighting light marker, whereby the sighting light coming from the sighting light source 71 is by the coupling lens 73 and the light conductor 72 coupled in the opposite direction to the measurement beam path into the light conductor L and is directed through the aperture plate 44, the coupling lens 43, here acting as an extraction lens, the pickup lens 42, here acting as a projection lens, and the redirecting prism 41 and within the measurement window F onto the measurement object where it produces the sighting light marker. The focal apertures 44a of the aperture plate 44 thereby limit the size of the sighting light marker exactly to the size of the measurement region then taken into consideration for the measurement. The aperture plate 44 therefore forms a common adjustable shutter structure for the pickup arrangement and the optical sighting arrangement. It is therefore apparent to the use, especially for small colour fields, how the device must be positioned in order to safely measure within the measurement field. The beam path of the sighting light between the redirecting prism 41 and the measurement window F is illustrated in FIG. 10 and referenced with VL.

A further aspect of the invention relates to the physical white reference (white tile) 80. It is, as already mentioned, positioned at the free end of the pivot arm 81 which itself slides directly on the base plate B and is rotatably supported coaxial to the mantle 20 and slightly forced against the base plate by a spring 26. Upon rotation of the mantle 20 in one direction, the pivot arm 81 is rotated like a drag indicator by way of non-illustrated pusher dog until the white reference 80 located thereon is located exactly above the measurement window F. A white reference measurement can then be carried out in this position. Upon rotation of the mantle in the opposite direction, the pivot arm is not dragged along so that the measurement window F remains free and the scanning of the measurement object can be carried out.

According to a preferred alternative embodiment, the handheld measurement device in accordance with the invention is constructed as a so-called Gonio measurement device which allows the illumination of the measurement object under two or more different defined angle of incidence ranges. The optical measurement unit MU is therefore equipped with one or more further pairs of illumination light sources and, if necessary, associated illumination light optics, which are constructed and positioned analogously to the described pair of illumination light sources 31a,31b and illumination optics 32a, 32b, but impinge the measurement object in the region of the measurement window F with illumination light of respectively another angle of incidence range. Typical angle of incidence ranges were already mentioned above. Two further illumination light sources 131b and 231b are included in FIG. 8. Alternatively, only one single illumination light source can be provided for each of the additional illumination angle ranges.

Figure 11:
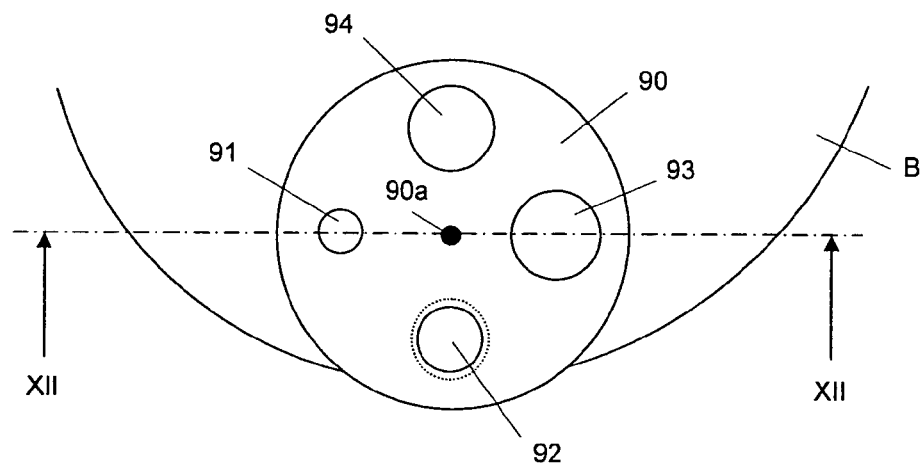
FIG. 11 a partial top view of a detail variant.
Figure 12:
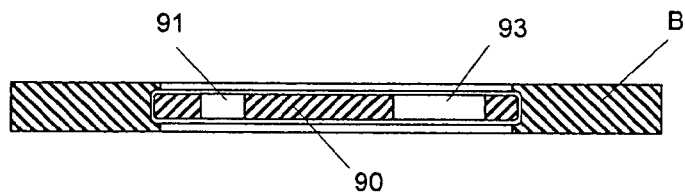
FIG. 12 a section taken along line XII-XII in FIG. 11.

An alternative embodiment of the measurement unit MU is schematically illustrated in FIGS. 11 and 12. An aperture wheel 90 is thereby provided instead of the measurement window F in the base plate B, which is supported for rotation in its plane about its axis 90a. The aperture wheel laterally slightly protrudes beyond the base plate B and preferably has a knurled edge so that it can be easily manually rotated. Several aperture openings 91 to 93 of different size are provided in the aperture wheel 90, which take on the role of the measurement window F and at the same time limit the measurement region. Additionally, a physical white reference 94 is positioned in or on the aperture wheel 90. By rotation of the aperture wheel 90, measurement regions of different size can be set or the white reference can be positioned in the measurement beam path.

According to a further advantageous embodiment, the handheld measurement device in accordance with the invention is provided instead of or in addition to the interface connector IF with a wireless communication interface which enhances the handling comfort. Suitable wireless communication interfaces are generally known and do not require any further description.

The handheld measurement device in accordance with the invention was described in the preceding by way of an exemplary spectrophotometer. It is however understood that the invention is not limited to spectrophotometers. Rather, the handheld measurement device can also be constructed as a classical colour or density measurement device, whereby then instead of the spectrometer unit SU a corresponding colour measurement unit or a density measurement unit would be present. Such colour and density measurement units (essentially a combination of measurement filters and suitable photoelectric converters) are generally known and do not require any further description for the person skilled in the art.

The invention claimed is:

1. Optical measurement unit for a measurement device for the photoelectric scanning of a measurement location of a measurement object, comprising:

an illumination arrangement (IU) for impinging of the measurement object (MO) with illumination light under a first defined, relatively small angle of incidence range ($\epsilon$) and with an optical pickup arrangement (PU) for capturing of measurement light remitted from the measurement object (MO) under a defined, relatively small pickup angle range ($\alpha$), wherein the illumination arrangement (IU) has a pair of illumination light sources (31a, 31b) which impinge the measurement object (MO) from different spatial directions under the same first angle of incidence range ($\epsilon$) with illumination light, whereby illumination beam paths (ILa, ILb) at least in the vicinity of the measurement object (MO) are offset to one another by an offset angle ($\phi$) of essentially 90° relative to an axis (AX) perpendicular to the measurement location, and wherein the optical pickup arrangement (PU) includes a redirecting prism (41), a pickup lens (42), a coupling lens (43), and an adjustable aperture means (44), whereby the coupling lens (43) feeds the measurement light received through the redirecting prism (41) and the pickup lens (42) through the adjustable aperture means (44) into a light conductor (L) and the adjustable aperture means (44) limits a captured measurement region (MS) on the measurement object.

2. Measurement unit according to claim 1, wherein the first angle of incidence range ($\epsilon$) extends essentially from 40 to 50°.

3. Measurement unit of according to claim 1, wherein the pickup angle range ($\alpha$) is essentially a range of one of: (i) −5° to +5° and (ii) +3° to +13°.

4. Measurement unit according to claim 1, wherein the illumination light sources (31a, 31b) can be selectively switched on and off.

5. Measurement unit according to claim 1, wherein the illumination arrangement (IU) is constructed for impinging the measurement object (MO) with illumination light selectively under the first and at least one further defined angle of incidence range.

6. Measurement unit according to claim 5, wherein the illumination arrangement (IU) for each further angle of incidents range has at least one illumination light source (131b, 231b) which impinges the measurement object (MO) with illumination light through respectively one associated illumination optic.

7. Measurement unit according to claim 5, wherein the illumination arrangement (IU) for each further angle of incidents range has a pair of illumination light sources (131b, 231b) which by way of an associated illumination optic impinge the measurement object (MO) with illumination light, whereby the illumination light sources (131b, 231b) of each pair are positioned in such a way and the associated illumination light optics are constructed in such a way that the illumination beam paths (ILa, ILb) are offset to one another at an offset angle ($\phi$) of essentially 90° in the vicinity of the measurement object (MO) relative to an axis (AX) perpendicular to the measurement location.

8. Measurement unit according to claim 1, further comprising one or more filters that can be brought into the beam paths of at least one of the illumination light and the measurement light.

9. Measurement unit according to claim 8, wherein the one or more filters are colour, density, UV or polarization filters.

10. Measurement unit according to claim 1, further comprising a physical white reference (80) that can be brought into the illumination and measurement beam paths.

11. Measurement unit according to claim 1, wherein the pickup arrangement (PU) includes means (41) for redirecting of the pickup measurement light by essentially 90°.

12. Measurement unit according to claim 1, wherein the pickup arrangement (PU) includes adjustable aperture means (44) for limiting of a captured measurement range (MS) of the measurement object.

13. Measurement unit according to claim 1, further comprising an optical sighting arrangement (71, 72, 73, 41, 42, 43, 44, L) which projects a sighting light point (VM) onto the measurement object (MO) which optically marks the position of the measurement region captured by the pickup arrangement (PU).

14. Measurement unit according to claim 1, further comprising an optical sighting arrangement (71, 72, 73, 41, 42, 43, 44, L) which projects a sighting light point (VM) onto the measurement object (MO) which optically marks the size of the measurement region captured by the pickup arrangement (PU).

15. Handheld photoelectric measurement device, comprising:
  a housing (G), which at its underside is provided with a measurement window (F) through which photoelectric measurement of a surface of a measurement object (MO) is carried out, with an optical measurement unit (MU) positioned in the housing, which optical measurement unit includes an illumination arrangement (IU) for impinging of the measurement object (MO) through a measurement window with illumination light under a first defined, relatively small angle of incidence range ($\epsilon$) and an optical pickup arrangement (PU) for capture of measurement light remitted from the measurement object (MO) through the measurement window under a defined, relatively small pickup angle range ($\alpha$), with a photoelectric converter arrangement (PEC) supplied by the optical pickup arrangement with the captured measurement light for conversion of the captured measurement light into corresponding electric measurement signals (DMS) and with an electronic processing arrangement (DCU) for the electric measurement signals,
  wherein the illumination arrangement (IU) has a pair of illumination light sources (31a, 31b), which impinge the measurement object (MO) from different spatial directions under the same first angle of incidence range ($\epsilon$) with illumination light, whereby illumination beam paths (ILa, ILb) at least in the vicinity of the measurement object (MO) are mutually offset by an offset angle ($\phi$) of essentially 90° relative to an axis (Ax) normal to the measurement location,
  wherein the housing (G) is provided with a lateral measurement space (N) which can be opened and closed to the outside by a movable wall portion (21), and wherein the measurement window (F) is located in the region of the measurement space (N) in such a way that the measurement window is freely visible to the user of the device when the measurement space is opened and wherein drive means (60) is provided for moving the wall portion (21) and thereby opening or closing the measurement space (N).

16. Handheld measurement device according to claim 15, wherein the measurement space (N) in the opened condition is open to the outside of the housing, but closed to the interior of the housing, whereby the interior of the housing is closed dirt and light tight.

17. Handheld measurement device according to claim 15, wherein within the housing (G) a tubular mantle (20) is provided having an essentially cylindrical portion (21) and an inwardly projecting indent or flat portion (22), which mantle is rotatably driven by a motor, the cylindrical portion (21) forming the movable wall portion of the housing (G) and opening or closing the measurement space (N) to the outside depending on the rotational position of the mantle (20).

18. Handheld measurement device according to claim 17, wherein the impinging of the measurement object (MO) with illumination light and capturing of the measurement light remitted from the measurement object occurs through the interior of the mantle (20).

19. Handheld measurement device according to claim 18, wherein in the interior of the mantle (20) at least one window plate (50) is positioned which is perpendicular to the rotational axis of the mantle and non-rotatably connected with the mantle (20), which window plate includes at least one illumination window (51) and at least one pickup window (52), which windows are positioned in such a way that they are located in a defined rotational position of the mantle (20) in the illumination beam path or in the pickup beam path of the illumination arrangement (IU).

20. Handheld measurement device according to claim 19, wherein a colour, density, UV or polarization filter is positioned in at least one of the illumination window (51) and the pickup window (52).

21. Handheld measurement device according to claim 20, wherein a physical white reference (80) is provided which is mechanically coupled with the mantle (20) and by a rotation of the mantle (20) is positionable in the region of the measurement window (F) or again removable from the region of the measurement window.

22. Handheld measurement device according to claim 15, further comprising a rotatable aperture wheel (90) with a number of differently sized focal apertures (91-93) for limiting the captured measurement region on the measurement object.

23. Handheld measurement device according to claim 22, wherein the aperture wheel (90) includes a white reference (94).

24. Optical measurement unit for a measurement device for photoelectric scanning of a measurement location of a measurement object, comprising
  an illumination arrangement (IU) for impinging of the measurement object (MO) with illumination light under a first defined, relatively small angle of incidence range ($\epsilon$) and with an optical pickup arrangement (PU) for capturing of measurement light remitted from the measurement object (MO) under a defined, relatively small pickup angle range ($\alpha$),
  wherein the illumination arrangement (IU) has a pair of illumination light sources (31a, 31b) which impinge the measurement object (MO) from different spatial directions under the same first angle of incidence range ($\epsilon$) with illumination light, whereby illumination beam paths (ILa, ILb) at least in the vicinity of the measurement object (MO) are offset to one another by an offset angle ($\phi$) of essentially 90° relative to an axis (AX) perpendicular to the measurement location, and
  an optical sighting arrangement (71, 72, 73, 41, 42, 43, 44, L);
  wherein the optical sighting arrangement (71, 72, 73, 41, 42, 43, 44, L) has a sight light source (71) optically coupled into the pickup arrangement (PU); and
  wherein projection of the sighting light marker (VM) onto the measurement object (MO) is carried out through the pickup arrangement (PU).

25. Optical measurement unit for a measurement device for photoelectric scanning of a measurement location of a measurement object, comprising
- an illumination arrangement (IU) for impinging of the measurement object (MO) with illumination light under a first defined, relatively small angle of incidence range ($\epsilon$) and with an optical pickup arrangement (PU) for capturing of measurement light remitted from the measurement object (MO) under a defined, relatively small pickup angle range ($\alpha$),
- wherein the illumination arrangement (IU) has a pair of illumination light sources (31a, 31b) which impinge the measurement object (MO) from different spatial directions under the same first angle of incidence range ($\epsilon$) with illumination light, whereby illumination beam paths (ILa, ILb) at least in the vicinity of the measurement object (MO) are offset to one another by an offset angle ($\phi$) of essentially 90° relative to an axis (AX) perpendicular to the measurement location, and
- an optical sighting arrangement (71, 72, 73, 41, 42, 43, 44, L), wherein the optical sighting arrangement (71, 72, 73, 41, 42, 43, 44, L) includes adjustable aperture means (44) for selling of different sizes of a sighting light marker (VM).

26. Measurement unit according to claim 25, wherein an adjustable aperture means (44) of the pickup arrangement (PU) operates at the same time as the adjustable aperture means (44) of the sighting arrangement (71, 72, 73, 41, 42, 43, 44, L).

* * * * *